US012491092B2

(12) United States Patent
Dmuschewsky et al.

(10) Patent No.: US 12,491,092 B2
(45) Date of Patent: Dec. 9, 2025

(54) TRIAL NECK PIECE FOR A JOINT ENDOPROSTHESIS

(71) Applicant: WALDEMAR LINK GmbH & Co. KG, Hamburg (DE)

(72) Inventors: Klaus Dmuschewsky, Hamburg (DE); Emel Altan, Düsseldorf (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 0 days.

(21) Appl. No.: 17/606,589

(22) PCT Filed: Apr. 24, 2020

(86) PCT No.: PCT/EP2020/061429
§ 371 (c)(1),
(2) Date: Oct. 26, 2021

(87) PCT Pub. No.: WO2020/216887
PCT Pub. Date: Oct. 29, 2020

(65) Prior Publication Data

US 2022/0233337 A1 Jul. 28, 2022

(30) Foreign Application Priority Data

Apr. 26, 2019 (EP) .................................... 19171459

(51) Int. Cl.
*A61F 2/46* (2006.01)
*A61B 17/16* (2006.01)
*A61F 2/36* (2006.01)

(52) U.S. Cl.
CPC .......... *A61F 2/4684* (2013.01); *A61B 17/164* (2013.01); *A61F 2002/3625* (2013.01)

(58) Field of Classification Search
CPC ............ A61F 2/4684; A61F 2002/3625; A61F 2002/30607; A61F 2002/30614;
(Continued)

(56) References Cited

U.S. PATENT DOCUMENTS 5,601,567 A * 2/1997 Swajger ................ A61F 2/3672
606/86 R
5,766,261 A * 6/1998 Neal .................. A61B 17/1659
606/85
(Continued)

FOREIGN PATENT DOCUMENTS

EP 0 145 641 A1 6/1985
EP 0 283 706 A1 9/1988
(Continued)

OTHER PUBLICATIONS

International Search Report and Written Opinion mailed Aug. 6, 2020 in corresponding International Application No. PCT/EP2020/061429 and the English Translation of the International Search Report.

(Continued)

*Primary Examiner* — Alvin J Stewart
(74) *Attorney, Agent, or Firm* — Chiesa Shahinian & Giantomasi PC

(57) ABSTRACT

A trial neck piece for a joint endoprosthesis is designed for temporary arrangement on a separate shaft body (60) that is insertable into a tubular bone (9). It comprises a fastening region (12) which can be plugged temporarily onto a head part (61) of the shaft body (60) by means of a plug connection (1 l), and a neck region (IO) for receiving a joint element (19) of the joint endoprosthesis. The trial neck piece (I) is designed as a separate, plug-on attachment piece which, with its fastening region (12), can be plugged with form-fit engagement onto the head part (61) and locked. A latching device (2) is provided which comprises a plurality of latching stages for different height stages of the trial neck piece (I). The invention thus makes available an easily attachable trial neck piece which can be arranged in a defined manner in different height positions in order, on the one hand, to obtain a secure and defined arrangement and, on
(Continued)

Figure 2:
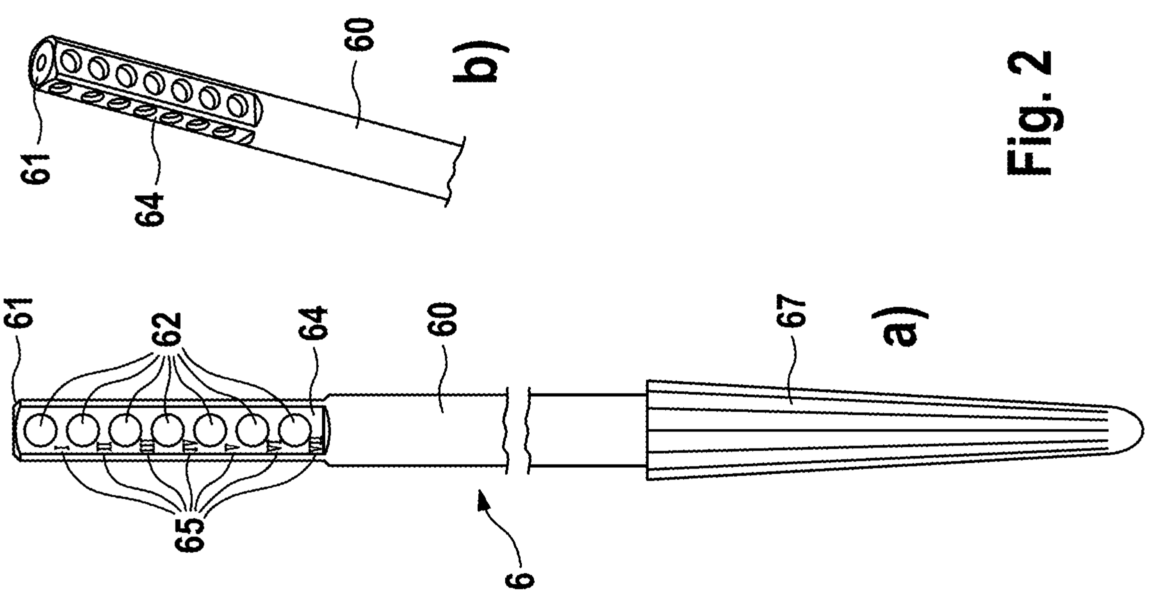

the other hand, to permit the setting of different heights. The invention further relates to an arrangement with a trial neck piece and with an excavating tool, in particular a reamer, and to an instrument set comprising a trial neck piece and an insertion instrument.

20 Claims, 6 Drawing Sheets

(58) Field of Classification Search
CPC . A61F 2002/30616; A61F 2002/30617; A61B 17/164
See application file for complete search history.

(56) References Cited

U.S. PATENT DOCUMENTS

| | | | | |
|---|---|---|---|---|
| 6,193,759 | B1 * | 2/2001 | Ro | A61F 2/4607 623/23.25 |
| 6,977,000 | B2 * | 12/2005 | Vanasse | A61F 2/4684 623/22.45 |
| 7,022,141 | B2 * | 4/2006 | Dwyer | A61F 2/4657 623/22.12 |
| 7,074,224 | B2 * | 7/2006 | Daniels | A61B 17/1668 606/80 |
| 7,235,106 | B2 * | 6/2007 | Daniels | A61F 2/4684 623/22.25 |
| 7,641,698 | B1 * | 1/2010 | Gibbs | A61F 2/4637 623/22.15 |
| 7,951,205 | B2 * | 5/2011 | McCleary | A61F 2/4684 623/23.15 |
| 8,449,619 | B2 * | 5/2013 | Metcalfe | A61F 2/4684 623/22.11 |
| 8,998,919 | B2 * | 4/2015 | Jones | A61B 17/164 606/102 |
| 9,439,785 | B2 * | 9/2016 | Huddle | A61F 2/4684 |
| 11,344,437 | B2 * | 5/2022 | Bailey | A61B 17/1659 |
| 11,602,359 | B2 * | 3/2023 | Clements | A61B 17/162 |
| 11,826,267 | B2 * | 11/2023 | Bushell | A61F 2/3609 |
| 11,931,268 | B2 * | 3/2024 | Board | A61F 2/3609 |
| 2004/0064186 | A1 * | 4/2004 | McCleary | A61B 17/1659 623/18.11 |
| 2004/0122440 | A1 * | 6/2004 | Daniels | A61F 2/4684 606/102 |
| 2006/0241625 | A1 * | 10/2006 | Metcalfe | A61B 17/162 606/79 |
| 2007/0112430 | A1 | 5/2007 | Simmen et al. | |
| 2015/0018961 | A1 * | 1/2015 | Huddle | A61F 2/4684 623/22.4 |
| 2016/0262912 | A1 * | 9/2016 | Burnikel | A61F 2/4684 |
| 2018/0185156 | A1 * | 7/2018 | McCleary | A61B 17/164 |
| 2018/0318089 | A1 * | 11/2018 | Carr | A61F 2/4684 |
| 2019/0117412 | A1 * | 4/2019 | Zimmerman | A61B 17/1668 |
| 2019/0282378 | A1 * | 9/2019 | Borries | A61F 2/4637 |
| 2020/0268528 | A1 * | 8/2020 | Perez | A61F 2/3662 |
| 2020/0352742 | A1 * | 11/2020 | Horne | A61F 2/4684 |
| 2022/0241092 | A1 * | 8/2022 | Board | A61F 2/3609 |
| 2022/0249256 | A1 * | 8/2022 | Amaral | A61F 2/4607 |
| 2022/0346976 | A1 * | 11/2022 | Naylor | A61F 2/3662 |

FOREIGN PATENT DOCUMENTS

| | | | | | |
|---|---|---|---|---|---|
| FR | 2 735 972 | A1 | | 1/1997 | |
| JP | 2013094331 | A | * | 5/2013 | A61F 2/4684 |
| WO | WO 2007/028832 | A2 | | 3/2007 | |
| WO | WO-2019034769 | A1 | * | 2/2019 | |
| WO | WO-2019057698 | A1 | * | 3/2019 | |
| WO | WO-2020124052 | A1 | * | 6/2020 | A61B 17/025 |
| WO | WO-2020193004 | A1 | * | 10/2020 | |
| WO | WO-2020193005 | A1 | * | 10/2020 | |
| WO | WO-2022229360 | A1 | * | 11/2022 | A61F 2/3609 |

OTHER PUBLICATIONS

Search Report dated Oct. 30, 2019 issued in corresponding European Application No. 19171459.1.

* cited by examiner

TRIAL NECK PIECE FOR A JOINT ENDOPROSTHESIS

CROSS-REFERENCE TO RELATED APPLICATIONS

This application is the National Stage entry under 35 U.S.C. § 371 of International Application No. PCT/EP2020/061429 filed on Apr. 24, 2020, published on Oct. 29, 2020 under Publication Number WO 2020/216887 A1, which claims the benefit of priority under 35 U.S.C. § 119 of European Patent Application Number 19171459.1 filed Apr. 26, 2019, the entireties of which are herein incorporated by reference.

The invention relates to a trial instrument set for a joint endoprosthesis, comprising in particular a trial neck piece which is designed for temporary arrangement on a separate shaft body that is insertable into a tubular bone.

Endoprostheses, in particular joint endoprostheses, require secure anchoring in the bone in order to be able to perform their function in a stable and reliable manner over the long term. Such joint endoprostheses therefore have a long shaft to permit better anchoring. This shaft must be securely fastened in the bone on which the joint endoprosthesis is to be arranged. In most cases, these are tubular bones, with the shaft being inserted into a medullary canal or another cavity to be made in the tubular bone. The space required in the bone is usually created by excavating, for example in the medullary canal of a femur, in particular by means of a reamer. After the excavating, a check is carried out to ascertain whether the width and depth of the cavity created are sufficient. This check is essential because it is crucial with regard to a correct fit of the joint endoprosthesis that is subsequently to be implanted.

It is known to use separate trial instruments and implants for this purpose. However, the use of separate trial instruments and implants involves additional effort, both in terms of preparing for the operation and in the subsequent cleaning after the operation.

In practice, therefore, there is often a move not to use separate trial instruments, and instead to use the instrument that was used for excavating the cavity (in most cases this is the reamer). The advantage here is that this instrument is already present in the cavity anyway, and it does not therefore need to be introduced separately. Moreover, any further working that may be needed can then be easily carried out by simply creating additional cavity with the reamer. This results in significant handling advantages. However, there is the disadvantage that instruments such as the reamer are not in themselves designed to function as a trial instrument. In the case of instruments such as the reamer, the main focus lies in the actual work purpose. Among other things, this is reflected by the fact that the reamer has at its upper end a drive head that protrudes quite far out of the bone (in order to be able to actuate the reamer from there). This large protrusion gets in the way during trials and makes precise examination or alignment more difficult.

In order to avoid this, systems have become known which have a relatively short reamer (or a two-part reamer, of which the upper part is removed), on the upper end of which a separate trial neck piece can be mounted. Since the height is different depending on the individual anatomy of the patient, intermediate pieces are provided in the known systems, or they comprise several trial neck pieces of different heights, from which a suitable one then has to be selected. Moreover, the known systems often require the individual elements to be screwed together. The handling of small parts, such as spacers or screws, is awkward and, in terms of the risk of loss, dangerous, and the use of several trial neck pieces of different heights is cumbersome.

The problem addressed by the invention is that of making available an improved instrument set that avoids these disadvantages.

The solution according to the invention lies in the features of the independent claims. Advantageous developments are the subject of the dependent claims.

In the case of a trial neck piece for a joint endoprosthesis, designed for temporary arrangement on a separate shaft body (in particular a reamer) that is insertable into a tubular bone, wherein the trial neck piece comprises: a fastening region which, by means of a plug connection, can be plugged temporarily onto a head part of the shaft body in at least one defined position (and removed therefrom), a neck region, which is designed to receive a joint element of a joint endoprosthesis, provision is made, according to the invention, that the trial neck piece is designed as a separate, plug-on attachment piece which, with its fastening region, can be plugged with form-fit engagement onto the head part and locked, wherein a latching device is provided which comprises a plurality of latching stages, preferably at least five latching stages, for different height stages of the trial neck piece on the head part of the shaft body.

Some of the terms used are explained below:

A free end of a tubular bone is understood to mean the end where the endoprosthesis is to be implanted. For example, when implanting a hip joint endoprosthesis, the proximal end of the femur is the free end of the tubular bone.

A drive head is understood to mean a coupling piece which is arranged at one end of a tool (for example a reamer) and on which driving forces act on this tool. A handle can be coupled for actuating the tool manually, and/or, if necessary, a machine drive.

Height stages are understood to mean different positions along a longitudinal axis of a shaft body. With a vertical orientation of the shaft body, this results in different heights for a combination of shaft body and trial neck piece.

The invention is based on the concept of making available an easily attachable trial neck piece that can be arranged in a defined manner at different height positions, in order on the one hand to thereby achieve a safe and defined arrangement and, on the other hand, to allow different heights to be set. It is therefore unnecessary to provide a plurality of trial neck pieces of different heights or to use separate parts for height adjustment, such as spacer rings. Additional plugging on or repositioning of other or further parts for height adjustment can thus be avoided according to the invention. By virtue of the latching, a secure and defined height adjustment is achieved, specifically at different heights defined by the latching stages. In this way, handling is not only much easier but also safer (since no further parts, in particular small parts, are needed, with the always immanent danger of these being mixed up or lost) and more reliable (since the latching stages ensure a quick and yet precise adjustment of the different heights).

There is also a further advantage, specifically with regard to better individual adaptation of the endoprosthesis to the anatomical conditions of the patient. This is because the attached and secured trial neck piece allows a swing movement of the joint (that is to say, for example in the implantation of a hip joint endoprosthesis, the thigh is moved from the extended to the drawn up position and back). In this way, it is possible to check whether a sufficient range of motion is guaranteed. If necessary, a different shaft length can be set by changing the height stage. This not only improves handling, it can also permit better overall adjustment of the endoprosthesis during the operation. The risk of incorrect implantation, which brings with it the danger of costly secondary operations that place a strain on the patient, can thus be effectively minimized.

A securing device is preferably provided, which secures the latching of the trial neck piece in the respective height stage. In this way, a simple, quick and reliable securing of the respectively set height is achieved, specifically without the need for separate parts such as spacer rings or the like. The latching device and/or securing device are advantageously self-locking. In this way, separate maneuvers for locking the latching device are not needed, and instead but they snap in automatically as it were. This results in considerably easier handling. This therefore also minimizes the danger of the latching device inadvertently not being locked.

A guide for a releasable quick coupling to an insertion instrument is expediently provided on the trial neck piece. In this way, the insertion instrument can be securely connected to the trial neckpiece in a simple and quick way. In particular, the connection is both tension-resistant and angularly stable, i.e. the relative angular position between the trial neckpiece and the insertion instrument is fixed.

In this case, the guide preferably has an angled guide track with an insertion portion and a locking portion, wherein the locking portion, seen from a beginning of the insertion portion, is designed as an undercut. The locking portion simplifies the insertion of the quick-release coupling, and the undercut design of the locking portion achieves a particularly secure connection that is intrinsically protected against unintended loosening.

The fastening region is advantageously designed to be plugged on with a turn-around, preferably with a rotation in 120° steps or less. “Turn-around” is understood to mean that the trial neck piece can be mounted in various rotational positions relative to a longitudinal axis of the trial neck piece, wherein the individual rotational positions are preferably defined by the outer contour of the upper region of the shaft.

It is preferred if the fastening region has, at its lower end, a shoulder which limits an insertion depth. In this way, it is possible to avoid the trial neck piece being pushed too far onto the shaft body.

The trial neck piece is expediently designed such that it is designed for screwless fastening to the shaft body. This permits a particularly simple and quick connection between the trial neck piece and the shaft body.

The fastening region is preferably designed as a sliding sleeve with a through-opening for plugging onto the shaft body, which sliding sleeve is preferably tiltable. The plugging on permits quick assembly, wherein the tiltability can be used to simplify the shifting of the trial neck piece from one height stage to another. In particular, provision can be made that a part of an inner wall of the through-opening is designed obliquely as a ramp. With this embodiment, a free space is made available in a particularly simple manner by means of the ramp, which free space allows the shaft to tilt within the through-opening.

It is particularly expedient if, at the through-opening, a latching lug is arranged which, in a locking position, engages in a depression of the shaft body and, in a tilting position, is free from the shaft body, wherein the latching lug is preferably arranged rigidly on the through-opening. This results in a form-fit connection between the trial neck piece on the one hand and the shaft body on the other hand, which permits a high degree of protection against unintended displacement. Moreover, this allows easy displacement in the tilting position. Preferably, the latching lug is arranged opposite the neck region. It can thus be achieved that, when a load is applied, that is to say in particular when a force is applied to the neck region, the latching lug is pressed into the depression. In this way, a self-locking action is obtained, the effectiveness of which is greater the higher the loading force. It has proven useful if the latching lug is arranged on the same side of the through-opening as the ramp. In particular, the latching lug is expediently arranged in the region of the beginning of the ramp in the through-opening. A particularly favorable configuration of the transition region toward the ramp can thus be achieved.

The trial neck piece advantageously has a pressure spring, preferably a leaf spring, which acts on the inserted shaft body. It is designed to press the trial neck piece into the locking position, such that simple and secure latching in the respective height stage is achieved. A blocking element is expediently provided for the pressure spring. It blocks a movement of the pressure spring such that the latter cannot deflect, and thus the trial neck piece is forced into the locking position.

In a preferred embodiment, a viewing window is provided which is arranged such that, with a shaft body inserted, it shows an identification field assigned to the respective latching position. The identification field is advantageously provided with a marker for a size and/or depth dimension. In this way, a simple visual check, using the marker appearing in the viewing window, can verify whether a desired setting has been achieved.

The danger of incorrect settings is therefore countered in a way that is as simple as it is effective. Provision is expediently made here that the identification field is provided with a marker for a size and/or depth dimension.

The separate shaft body is preferably designed as an excavating tool, in particular a reamer. As has already been noted in the introduction, a reamer (or another excavating tool) is particularly suitable as a shaft body for the trial neck piece according to the invention.

The invention also extends to an arrangement comprising the trial neck piece and such an excavating tool, in particular a reamer. A standard attachment for surgical instruments, preferably a Hudson attachment, is preferably configured at the upper end of the excavating tool. Additionally or alternatively, the excavating tool, in particular the reamer, can also be designed in two parts with a proximal and a distal part, which are both connected captively in an angularly articulated and rotationally fixed manner. This results in the excavating tool, in particular the reamer, having a design that is particularly favorable for surgical practice.

The invention moreover extends to an instrument set comprising a trial neck piece as explained above and also an insertion instrument which, at its distal end, is provided with a releasable quick coupling for receiving the trial neck piece at a fixed angle. The insertion instrument preferably has, at its front end, a gripping module with a rigid receiving fork, and with a clamping body which is arranged in a longitudinally displaceable manner at the base of the receiving fork and which is preferably also fork-shaped. With such a combination of fork and clamping body, the trial neck piece can be safely and easily gripped with particularly simple handling and can be reliably tensioned and secured against undesired movement.

The clamping body is advantageously actuated by means of a sliding member, which is preferably part of a fixing device. Here, the fixing device is preferably of a bi-stable design, preferably by means of a beyond-dead-center mechanism, more preferably with two stops for the gripping and releasing positions. With the beyond-dead-center mechanism, the fixing device can be easily switched between the opened and the closed (fixed) position. There are only two stable positions, which counteracts the danger of wrong conditions. There are therefore considerable handling advantages for the instrument.

The sliding member is expediently designed as a spring rod. In this way, on the one hand, clamping forces can be exerted on the clamping body and, on the other hand, there is an automatic clearance compensation, such that the trial neck piece can be securely retained even in the event of unavoidable tolerances in respect of its dimensions.

According to a further preferred embodiment, the invention also extends to an instrument set comprising an adapter piece which, subsequent to the trial neck piece, can be placed onto the shaft body and latched onto the latter. With the aid of this adapter piece, the shaft body, in particular the reamer, can be easily extracted from the medullary canal. Here, the same latching mechanism is preferably used as in the latching device of the trial neck piece.

Figure 1:
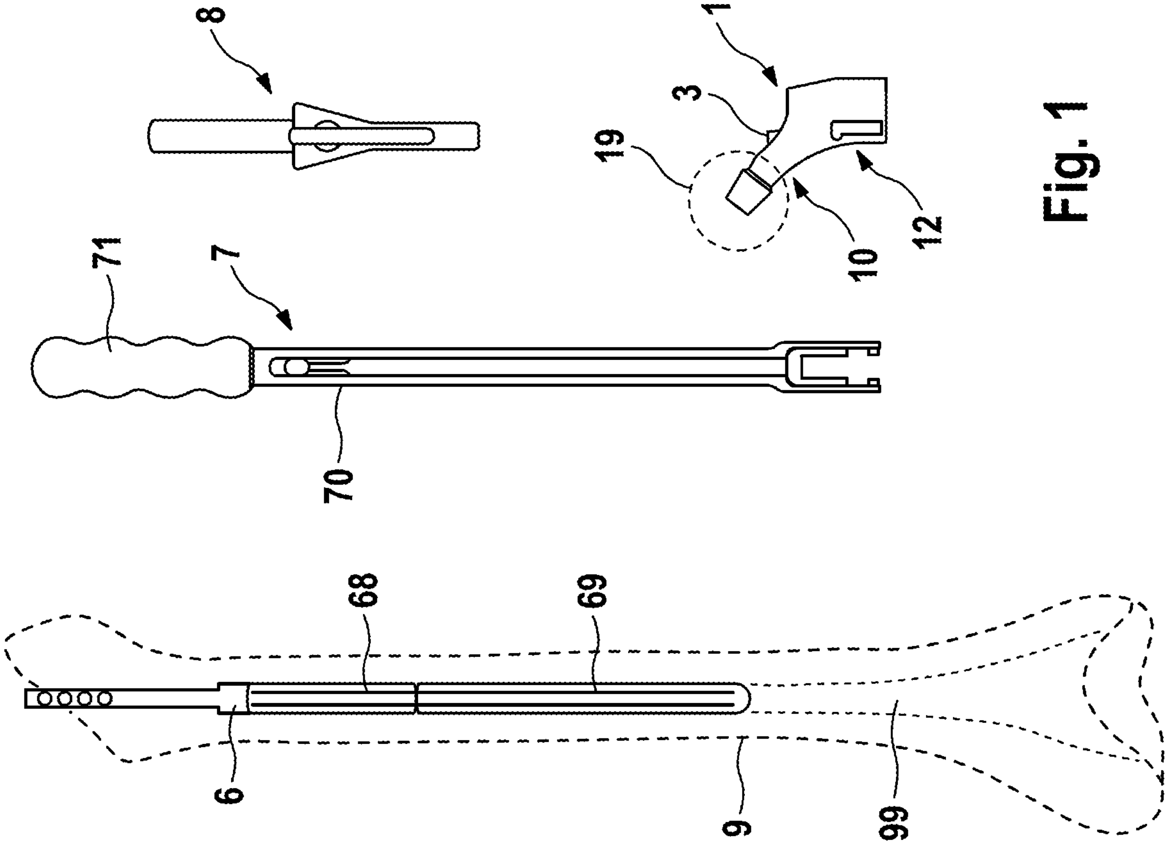
Figure 3:
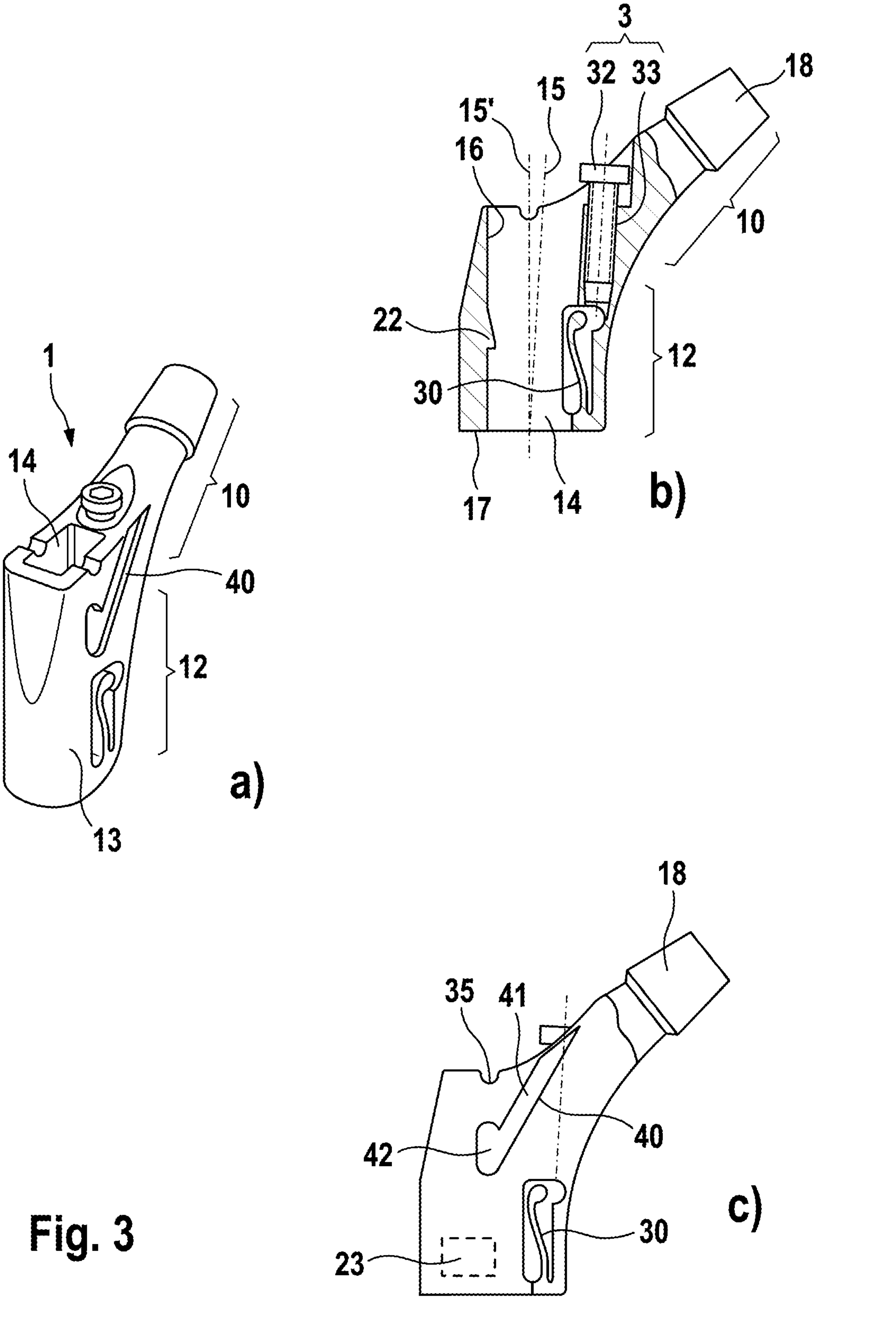
Figure 5:
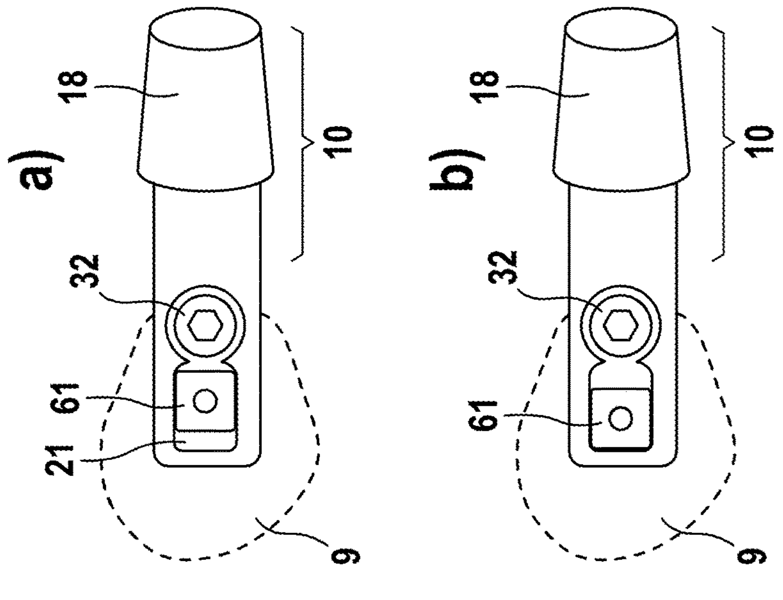
Figure 8:
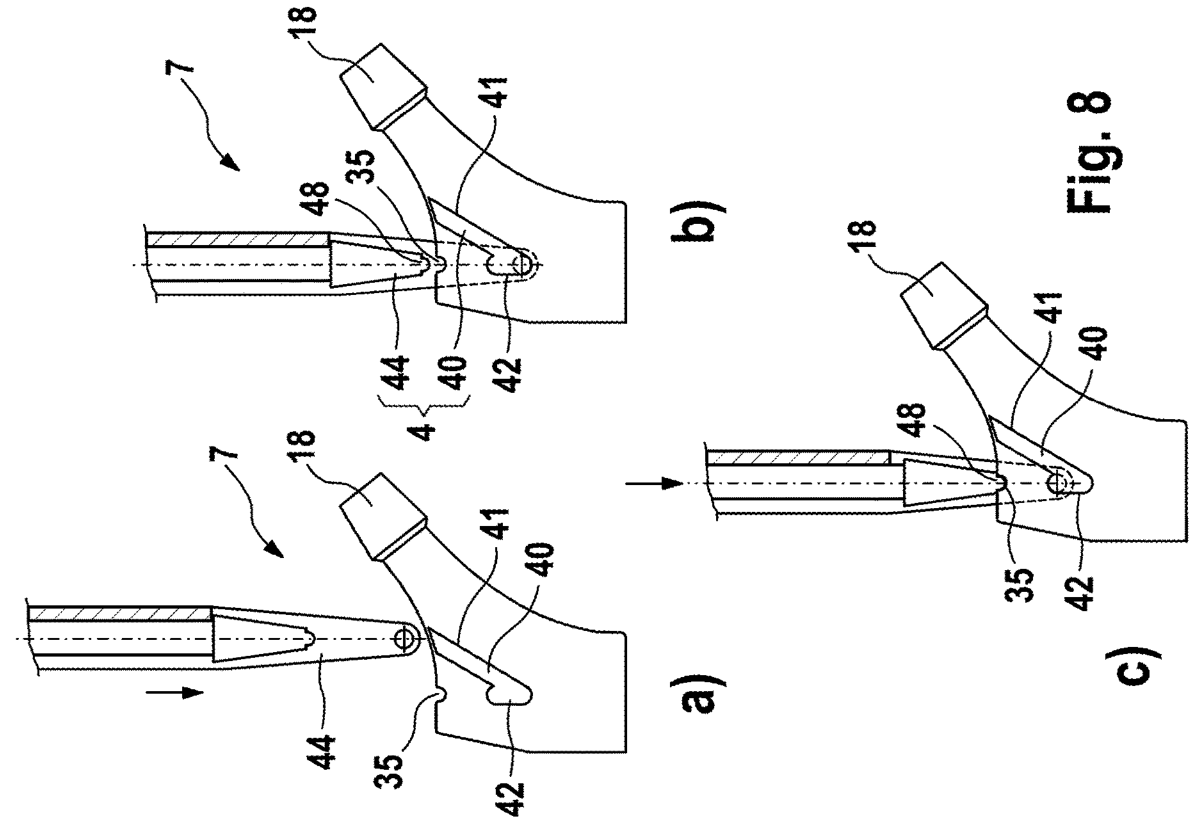
Figure 7:
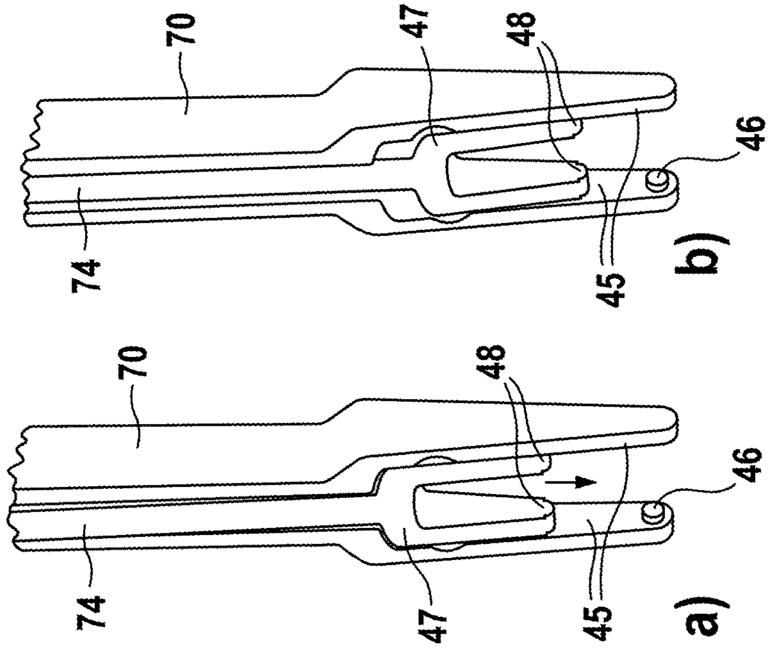
Figure 9:
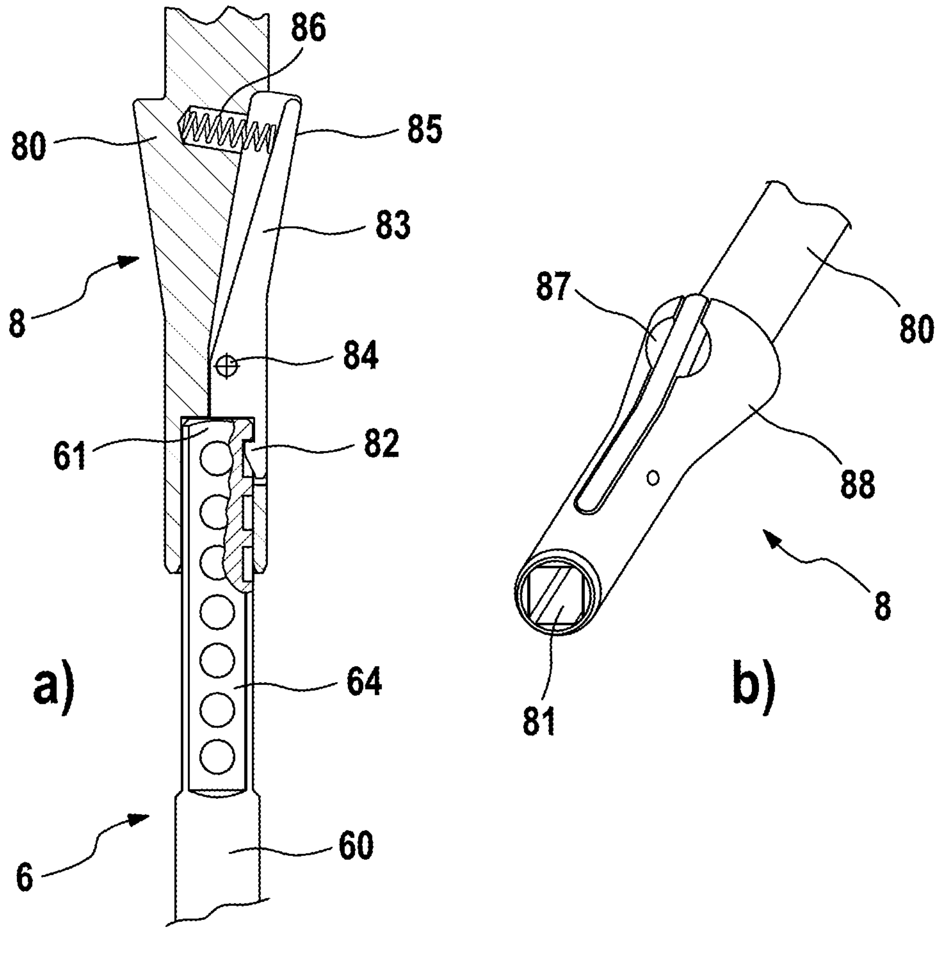

The invention is explained in more detail below on the basis of advantageous exemplary embodiments and with reference to the drawing, in which:

FIG. 1 shows an overview of an instrument set for excavating and testing;

FIGS. 2*a, b* show detailed view of a reamer according to one embodiment of the invention;

FIGS. 3*a-c* show views of a trial neck piece according to one embodiment;

FIGS. 4*a-d* show a trial neck piece in different positions, with and without latching or securing;

FIGS. 5*a, b* show a plan view of the trial neck piece depicting a transition and a locked position;

FIGS. 6*a-c* show several views of an insertion instrument for the trial neck piece;

FIGS. 7*a, b* show views of a gripper of the insertion instrument, in the open state and locked state;

FIGS. 8*a-c* show views of different phases in the coupling of the trial neck piece to the insertion instrument; and FIGS. 9*a, b* show views of an extraction adapter for the reamer.

An exemplary embodiment of an instrument set with a trial neck piece according to an exemplary embodiment of the invention is explained below. An overview of such an instrument set is shown in FIG. 1. This is an instrument set for inserting a femoral component of a hip joint endoprosthesis (not shown) into the proximal end of a femur 9. Here, the femoral component has an elongate shaft for anchoring in a cavity of the femur 9. For this purpose, a medullary channel 99 naturally present in the femur is widened by means of the instrument set in order to accommodate the shaft of the femoral component.

The depicted embodiment of an instrument set according to the invention comprises a trial neck piece 1, a reamer 6, an insertion instrument 7 for the trial neck piece 1, and an extraction adapter 8. Further instruments can be provided, in particular instruments that are usually part of an instrument set for implanting a hip joint endoprosthesis, in particular the femoral component thereof.

The reamer 6 is designed to widen the medullary canal 99 in the femur 9 at its proximal and adjoining medial diaphyseal region. This is done by excavation, wherein bone substance is removed from the interior of the femur 9 by means of a cutting region 67 of the reamer 6.

Optionally, other instruments can also be used before the reamer 6, such as a bone saw for removing a defective neck of the femur 9, and drills or other suitable tools for opening an access to the medullary canal 99 of the femur 9.

The excavation itself can take place in one or more steps, if appropriate also using different reamers (not shown) of progressively increasing size. At the end of the actual excavation, a check has to be made to ascertain whether the medullary canal 99 has been sufficiently widened. This trial is often carried out conventionally using a separate trial implant. According to the invention, this is no longer necessary. Instead, according to the invention, the reamer 1 used for the excavation and present anyway in the medullary canal 99 is used. For this purpose, the reamer 1 can remain in its position; it now functions with its shaft body 60 as the shaft of a trial implant.

The trial neck piece 1 essentially imitates the neck region of a trial implant. In other words, it corresponds substantially to a trial implant without its shaft. The trial neck piece 1 has a fastening region 12, which is designed for arranging the trial neck piece 1 on the shaft body 60, and a neck region 10, which is designed like a conventional neck region of a trial implant or of an implant. The neck region 10 is designed to carry a joint element (joint ball 19) of the joint endoprosthesis. To carry the joint ball 19, a receiving cone 18 is preferably formed in a manner known per se on the neck region 10, at the outer end thereof. The joint ball 19 can therefore be mounted with the same geometry as in the final joint endoprosthesis, and the joint can thus be moved using the joint endoprosthesis, so as to check the correct fit of the prosthesis and the mobility of the limbs. This procedure is also referred to as testing. If it turns out that the fit is not optimal, for example because the free space in the medullary canal 99 has not yet been made sufficiently deep, this can then be corrected by further excavation of the medullary canal 99 and easily checked, without for this purpose having to remove the reamer 6 or without even having to use the final joint endoprosthesis.

For testing, the trial neck piece 1 according to the invention is placed onto the shaft body 60 of the reamer 6. For this purpose, the trial neck piece 1 has a main body, designed as a sliding sleeve 13, with a through-opening 14. The trial neck piece 1 is plugged with its through-opening 14 onto a head part 61 of the shaft body 60 of the reamer 6. This head part 61 of the shaft body is formed as a square 64. The square 64 functions as a drive head of the reamer 6. The trial neck piece 1 is thus fastened to the shaft body 60 with form-fit engagement, such that no relative twisting can occur between the trial neck piece 1 and the shaft body 60. How far the trial neck piece 1 can be plugged onto the shaft body 60 of the reamer 6 is variable. A number of height stages are provided for this purpose, such that the plug-on depth of the trial neck piece 1 on the shaft body 60 can be varied. In this way, different lengths of trial implants can be simulated depending on the selected height stage. To limit the insertion depth, a shoulder 17 is provided at the lower end of the fastening region 12 of the trial neck piece 1.

For the different height stages, a plurality of latching holes 62 are arranged in a row along the axis of the shaft body 60 on top of the head part 61, on at least one side of the square 64. The arrangement of the latching holes 62 is preferably located on several sides of the square 64, in order to allow the trial neck piece 1 to be rearranged ("turned around") with respect to its angular position (in 90° steps in the case of a square). Moreover, identification fields 65 assigned to the latching holes 62 are provided on one side of the square 64. These preferably carry markers for the various latching steps 20, in the example shown I-VII for the seven height stages defined by the seven latching holes 62. A corresponding viewing window 21 is provided on the trial neck piece 1. It is designed as a cutout and permits, from the outside, a view of the side face of the square 64 that is provided with the identification fields 65. The identification field 65 corresponding to the respective latching hole 62 thus appears with its marking in the viewing window 21, such that in this way the height stage that has been set can be read off easily and cannot be mixed up.

For interaction with the latching holes 62, a latching lug 22 is provided on an inner side of the through-opening 14. In the exemplary embodiment shown, the latching lug 22 in the through-opening 14 is arranged on the side face opposite the neck region 10. The latching lug 22 is designed like a sawtooth with an inclined upper region and with a steep lower region (see FIG. 3*b*). The oblique upper region makes it easier for the latching lug 22 to engage in one of the latching holes 62, while the steep lower region acts as an abutment shoulder in the latched state, and therefore a high force can be safely transmitted between the trial neck piece 1 and the shaft body 60 of the reamer 6. This steep design of the abutment shoulder means that there is no risk of the latching lug 22 springing out of the latching hole 62 in an desired manner, even under a high force. Thus, the latching lug 22 and in each case one of the latching holes 62 together form a latching step 20 of a latching device 2. In the exemplary embodiment shown, the number of latching steps 20 corresponds to the number of latching holes 62. Thus, by moving the trial neck piece 1 on the square 64 and engaging it in one of the latching holes 62, a defined height of the trial neck piece 1 relative to the shaft body 60 of the reamer can be adjusted and locked securely. In this way, different sizes of implants can be simulated using one and the same reamer 6 or trial neck piece 1.

In order to promote a quick and secure engagement of the latching lug 22 in the respective latching hole 62, a pressure spring 30 designed as a leaf spring is also provided in the through-opening 14. It is arranged on the inner face of the through-opening 14, specifically on the inner face lying opposite the latching lug 22. The pressure spring 30 thus acts on the opposite surface of the square 64 and thus presses it overall in the direction of the latching lug 22. A secure engagement between the latching lug 22 and the corresponding latching hole 62 is thereby promoted. In this way, the latching device 2 almost automatically latches into place as soon as the trial neck piece 1 has been pushed along the shaft body 60 into the appropriate position. This latched state is depicted in FIGS. 4*a* and 4*c*.

Figure 4:
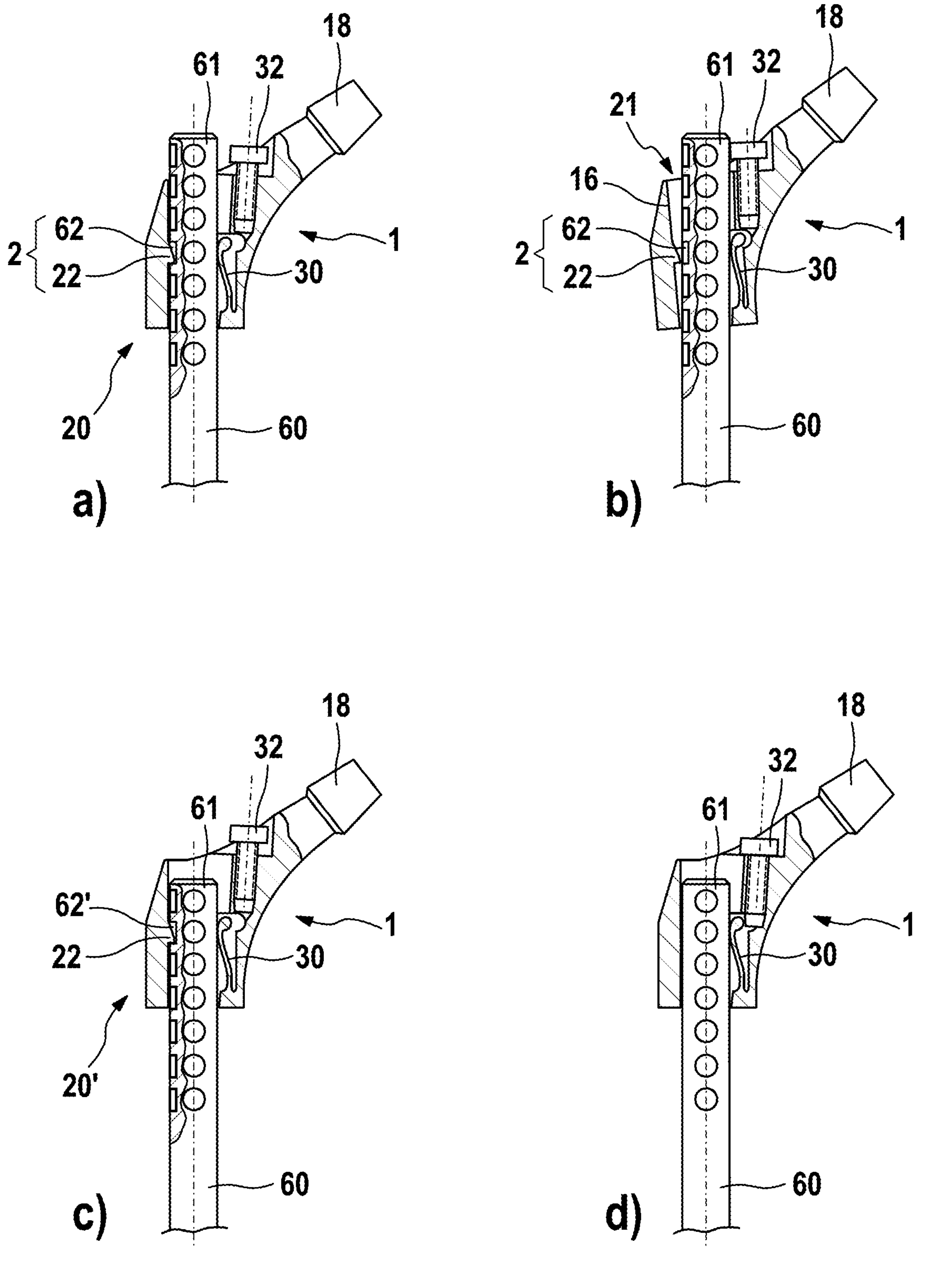

The shift between different latching holes 62 is visualized in FIG. 4*b*. It will be seen that the latching lug 22 does not engage in one of the latching holes 62 but instead sits on the outer surface of the square 64 (or slides along it when moving). It will also be seen that the trial neck piece 1 is positioned with a tilt in relation to the latched position (compare FIGS. 4*a* and 4*c*). This tilting makes it possible that the latching lug 22 is located outside the latching holes 62, and thus the trial neck piece 1 can be easily displaced along the square 64 of the shaft body 60. In order to facilitate this, a recess designed as an inclined ramp 16 is provided in the through-opening 14, on the same side on which the latching lug 22 is also arranged. As can be seen particularly clearly in FIG. 3*b*, at this point the wall of the through-opening 14 is not parallel to the opposite side, but rather tilts by a certain angle. This can also be seen from the dashed line, wherein the continuous vertical line represents the central axis 15 of the through-opening 14, and the resulting tilting on account of the ramp 16 is visualized by the line 15' located to the left of it and tilted by a few degrees. The trial neck piece 1 can be tilted by the resulting angular amount when moving from one latching hole 62 to another of the latching holes 62, as is shown in FIG. 4*b*. When the desired latching hole 62' is reached, the trial neck piece 1 is tilted back under the action of the pressure spring 30 to the original position, i.e. parallel to the central axis 15, wherein the latching lug 22 engages in the latching hole 62'. The latching device 2 is thus locked in another latching stage 20' with respect to an undesired longitudinal movement of the trial neck piece 1 along the shaft body 60.

To provide additional protection of the latching device 2 against undesired movement or actuation, a securing device 3 is additionally provided. In the exemplary embodiment shown, it is designed as a locking screw 32 in a secondary bore 33. The locking screw 32 is arranged in the transition between the neck region 10 and the fastening region 12 of the trial neck piece 1, and the secondary bore 33 is preferably adjacent to the through-opening 14 and is arranged approximately parallel, wherein the secondary bore 33 ends in the region of the pressure spring 30. By screwing in the locking screw 32, the shank of the latter is moved down so far that at least the tip of the shank of the locking screw 32 pushes the pressure spring 30 against the side faces of the square 64 of the shaft body 60 and thus jams the shaft body 60 in its untilted position in the through-opening 14 of the trial neck piece 1. Tilting is therefore no longer possible, such that the latching lug 22 is caught in the corresponding latching hole 62 and a longitudinal movement of the latching device 2 is reliably blocked. By unscrewing the locking screw 32, this locking can be released again if desired.

In order to allow the surgeon to easily check from the outside whether the latching device 2 is securely engaged, a test window 21 is provided. The latter is formed at the upper end of the trial neck piece 1 (see FIG. 5*a*), specifically between the upper end 61 of the shaft body 60 and that side of the trial neck piece 1 facing away from the neck region 10. The test window 21 is visible when the trial neck piece 1 is in the tilted state, as is also depicted in FIG. 4*b*. When this test window 21 is visible, the latching device 2 is not engaged and there is therefore an unsecure state. It is only when the trial neck piece 1 has once again adopted its untilted state (see FIG. 5*b*) that the test window 21 disappears. This is the sign that the latching device 2 is now engaged again. Now, if so desired, the locking screw 32 can be screwed in for further securing, so as to achieve the secured state according to FIG. 4*d*.

For inserting the trial neck piece 1 and, if necessary, extracting the trial neck piece 1 together with the reamer 6, an insertion instrument 7 is provided. The latter is designed with a long shaft 70, at one end of which a handle 71 is arranged. At the opposite end of the shaft 70, a quick-release coupling 4 is provided which includes a gripping module 44. The gripping module 44 comprises a receiving fork 45, on each of whose mutually facing inner surfaces a retaining pin 46 is arranged. In the exemplary embodiment shown, the retaining pins 46 are formed as cylinder-like projections. The gripping module further comprises a clamping slide 47 which is arranged between the inner surfaces of the receiving fork 45 in such a way as to be displaceable in the longitudinal direction of the shaft. The clamping slide 47 is shaped like a fork at its end remote from the shaft, with pressure lugs 48 provided at the tip. On the shaft side, the clamping slide 47 is arranged on a sliding member 74 which is designed as a sliding pin and which is guided longitudinally displaceably along a central axis 72 of the shaft 70 of the insertion instrument 7. The sliding member 74 is preferably designed as a spring rod.

The gripping module 44 is designed to interact with a guide track 40 on the trial neck piece 1. The guide track is angled, with an elongate insertion portion extending from the upper edge obliquely in the direction of the central axis 15, and with a locking portion 42 which adjoins the far end of the insertion portion and extends like an undercut in the direction of the upper edge of the trial neck piece 1. The guide track 40 is dimensioned to accommodate the retaining pins 46. These can be pushed along the insertion portion 41 onto the main body of the trial neck piece 1 (see FIG. 8*a*) in order finally to adopt a holding position in the undercut locking portion 42 (see FIG. 8*b*). The pressure lugs 48 can then be brought to bear on the upper side of the trial neck piece 1. For this purpose, a pressure saddle 35 is preferably provided, having a concavity adapted to the outer contour of the pressure lugs 48. Thus, by bracing the clamping slide 47 with its pressure lugs 48 against the retaining pins 46, the trial neck piece 1 can be securely held on the insertion instrument 7, namely in a secure manner with respect to firm locking both in the longitudinal direction and against tilting (see FIG. 8*c*).

Figure 6:
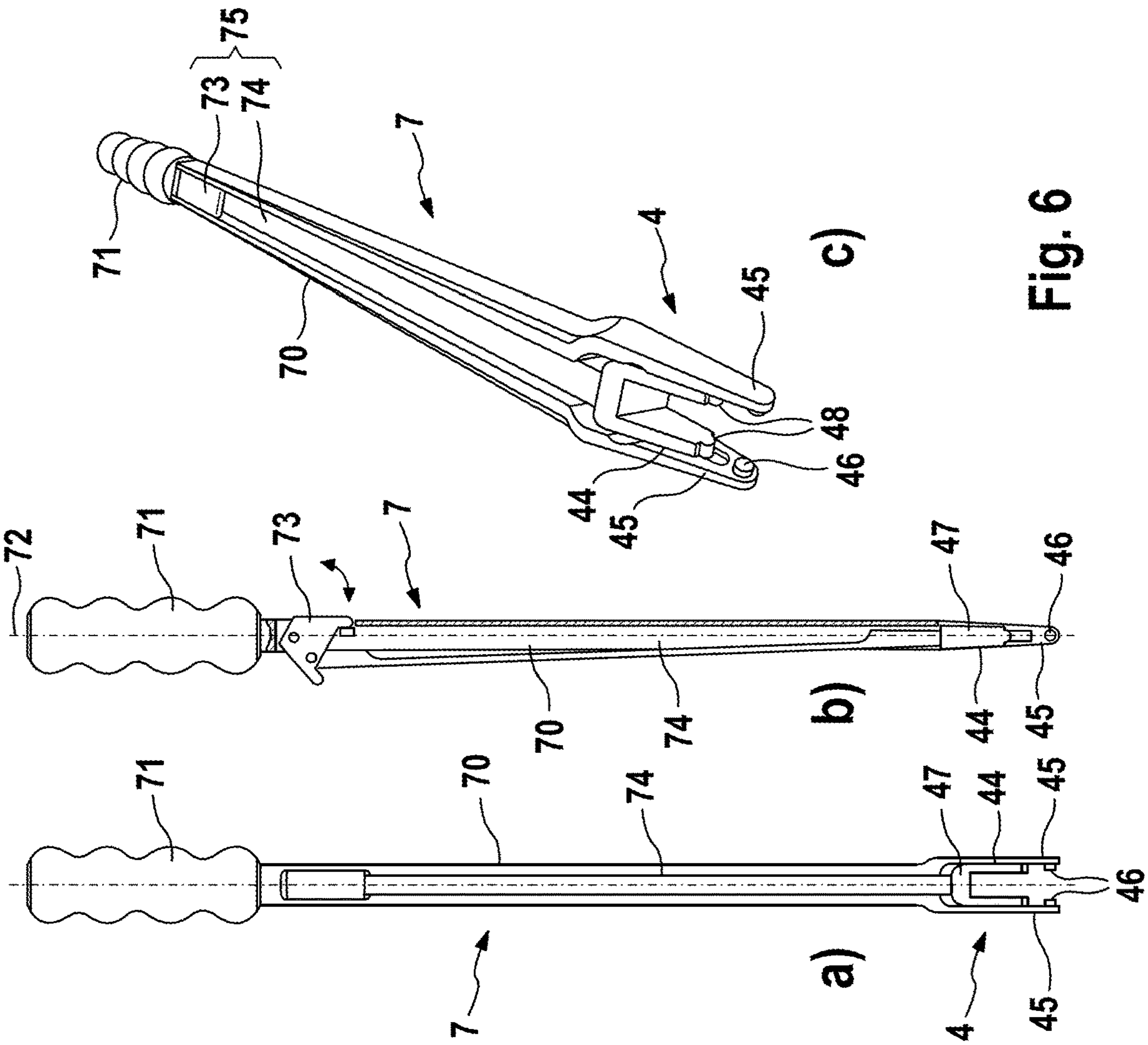

The sliding member 74, designed as a spring rod, forms, together with a pivot element 73, a beyond-dead-center mechanism (see FIG. 6). This represents a bi-stable fixing device for the gripping module 44. The front of the pivot element 73 acts on the sliding member 74 and moves the latter forward depending on a pivoting position. The clamping slide 47 arranged at the front end of the sliding member 74 is thus advanced accordingly (see also the arrow in FIG. 7*a*). The pivot element 73 has two stops, which each define an end position. In one end position, the sliding member 74 is drawn back with the clamping slide 47, and in the other end position the sliding member 74 is located with the clamping slide 47 in the advanced position. The pivot element 73 thus forms with the sliding member 74 a beyond-dead-center mechanism, with which the clamping slide 47 can be fixed in the advanced position and, by virtue of the sliding member 74 being made of spring steel, can be tensioned.

The actuation of the pivot element 73 and tensioning of the sliding member 74 occur when the gripping module 44 with its retaining pins 46 has been inserted into the guide track 40 on the trial neck piece 1 and the retaining pins 46 have adopted their position in the locking portion 42. By means of tensioning, the clamping slide 47 is then moved forward, such that it acts with its pressure lugs 48 on the pressure saddle 35, and the trial neck piece 1 is firmly gripped and held. It can thus be safely moved and positioned by means of the insertion instrument 7. This fastening is secure and capable of such high force transmission that, if appropriate, the reamer 6 coupled to the trial neck piece 1 via the locking device 2 can also be reliably extracted from the medullary canal 99 of the bone 9 by means of the insertion instrument 7.

The instrument set can furthermore comprise an extraction adapter 8. The latter is designed to be plugged onto the upper end 61 of the shaft body 60 of the reamer 6. The extraction adapter 8 has a shaft 80, at the front end of which a coupling piece is arranged. The coupling piece comprises a conical widening 88. At the front, free end of the extraction adapter 8, a square receiving opening 81 is provided. The latter is designed to receive the free end 61 of the shaft body 60. A locking device 83 is provided on one side of the receiving opening 81. The locking device 83 is designed as a lever which is pivotable via a bearing pin 84. At its far end, the lever of the locking device 83 has a retaining lug 82, which protrudes into the receiving opening 81. The retaining lug 82 is designed to interact with one of the latching holes 62 on the square 64 of the shaft body 60 of the reamer 6 in order to fix the reamer 6 with tension resistance on the extraction adapter 8. A pressure spring 86, which acts on an actuating lever 85 of the locking device 83, is arranged in the region of the thickening 88. It is pretensioned in such a way that it presses the actuating lever 85 into such a position that the retaining lug 82 is moved in the direction of the latching hole 62 and thus locked. The reamer 6 is thus retained on the extraction adapter 8 in a tension-resistant manner and can be pulled out of the bone 9 in a manner known per se. To release the extraction adapter 8, it is necessary only to exert pressure on the actuating lever 85 in order to pivot the retaining lug 82 out of the region of the receiving opening 81 and thereby release the reamer 6. For simple actuation, a recess 87 in the conical widening 88 is provided as a finger rest around the actuating lever 85.

At the opposite end of the shaft 80, the extraction adapter 8 preferably has an adapter for connection to conventional instruments, for example what is called a Hudson adapter (not shown). Thus, conventional tools can also be used to safely extract the reamer 6. Alternatively and/or in addition, provision can also be made for such a Hudson adapter to be arranged at the upper end of the head part 61 of the reamer, as long as the cross section thereof is small enough for passage through the through-opening 14 of the trial neck piece 1.

The invention claimed is:

1. A trial neck piece for a joint endoprosthesis, the trial neck piece comprising:

a fastening region configured to plug temporarily onto a head part of a shaft body in at least one defined position, a neck region, designed to receive a joint element of a joint endoprosthesis; and a securing device configured to secure the trial neck piece in the respective height stage on the head part of the shaft body, wherein the latching device or the securing device is self-locking, wherein the trial neck piece is configured to be plugged with form-fit engagement onto the head part and locked, wherein a latching device is provided which comprises a plurality of latching stages, for different height stages of the trial neck piece on the head part of the shaft body.

2. The trial neck piece of claim 1, wherein the trial neck piece comprises a guide configured to couple to an insertion instrument, and wherein the trial neck piece is configured for screwless fastening to the shaft body.

3. The trial neck piece of claim 2, having an angled guide track, with an insertion portion and a locking portion designed as an undercut.

4. The trial neck piece of claim 1, having a fastening region with a turn-around and said fastening region having a lower end, and a shoulder which is configured to limit insertion depth.

5. The trial neck piece of claim 1, having a fastening region comprising a sliding sleeve with a through-opening configured to plug onto the shaft body, wherein the sliding sleeve is tiltable, and wherein an inner wall of the through-opening comprises a ramp.

6. The trial neck piece of claim 5, comprising a through-opening, having a latching lug wherein when in a locking position, said latching lug engages in a depression of the shaft body and, in a tilting position, is free from the shaft body, wherein the latching lug is arranged on the through-opening.

7. The trial neck piece of claim 6, comprising a latching lug opposite the neck region such that, when force is applied to the neck region, the latching lug is configured to press into the depression, and the latching lug is on the same side of the through-opening as the ramp.

8. The trial neck piece of claim 1, comprising a pressure spring, which is configured to act on the shaft body, in an inserted configuration, and is configured to press the trial neck piece into a latched position.

9. The trial neck piece of claim 1, comprising a viewing window having an identification field wherein the identification field indicates a size or depth dimension.

10. The trial neck piece of claim 1, comprising a separate shaft body wherein attachment of surgical instruments is provided and the separate shaft body comprises a proximal and a distal part connected in an angularly articulated and rotationally fixed manner.

11. An instrument set comprising the trial neck piece of claim 1 and an insertion instrument comprising a distal end for coupling the trial neck piece at a fixed angle.

12. The instrument set of claim 11, further comprising an insertion instrument having a front end, a gripping module with a rigid receiving fork, and a clamping body arranged in a displaceable manner at a base of the receiving fork.

13. The instrument set of claim 12, further comprising a clamping body that is configured to be actuated by a sliding member.

14. The instrument set of claim 13, comprising a beyond-dead-center mechanism.

15. An instrument set for implanting a prosthesis, comprising:

a reamer configured to remove bone substance, having a head part, and a trial neck piece having a fastening region, which can be coupled to the head part of the reamer, and a prosthesis neck region designed to receive a joint ball of the prosthesis, wherein a drive head of the reamer is a polygon, and wherein the trial neck piece is configured to be plugged with form-fit engagement onto the drive head, and a latching device comprising a plurality of latching stages such that the trial neck piece is attached at different heights on the reamer.

16. The instrument set of claim 15, comprising the trial neck piece of claim 1.

17. A trial neck piece for a joint endoprosthesis, the trial neck piece comprising:

a fastening region configured to plug temporarily onto a head part of a shaft body in at least one defined position, a neck region, designed to receive a joint element of a joint endoprosthesis, wherein the trial neck piece is configured to be plugged with form-fit engagement onto the head part and locked, wherein a latching device is provided which comprises a plurality of latching stages, for different height stages of the trial neck piece on the head part of the shaft body, and wherein the fastening region comprises a turn-around and said fastening region has a lower end, and a shoulder which is configured to limit insertion depth.

18. The trial neck piece of claim 17, further comprising a securing device configured to secure the trial neck piece in the respective height stage on the head part of the shaft body, wherein the latching device or the securing device is self-locking.

19. A trial neck piece for a joint endoprosthesis, the trial neck piece comprising:

a fastening region configured to plug temporarily onto a head part of a shaft body in at least one defined position, a neck region, designed to receive a joint element of a joint endoprosthesis; and a pressure spring, which is configured to act on the shaft body, in an inserted configuration, and is configured to press the trial neck piece into a latched position, wherein the trial neck piece is configured to be plugged with form-fit engagement onto the head part and locked, and wherein a latching device is provided which comprises a plurality of latching stages, for different height stages of the trial neck piece on the head part of the shaft body.

20. The trial neck piece of claim 19, further comprising a securing device configured to secure the trial neck piece in the respective height stage on the head part of the shaft body, wherein the latching device or the securing device is self-locking.

* * * * *